US011337607B2

(12) United States Patent
Jaiprakash et al.

(10) Patent No.: US 11,337,607 B2
(45) Date of Patent: May 24, 2022

(54) OPHTHALMIC IMAGING APPARATUS AND SYSTEM

(71) Applicant: Integral Scopes Pty Ltd., Brisbane (AU)

(72) Inventors: Anjali Jaiprakash, Brisbane (AU); Douglas Palmer, Brisbane (AU); Donald Gilbert Dansereau, Sydney (AU); Thomas Coppin, Brisbane (AU); Krishan Rana, Brisbane (AU); Jonathan Roberts, Brisbane (AU); Ross Crawford, Brisbane (AU)

(73) Assignee: Integral Scopes Pty Ltd., Brisbane (AU)

( * ) Notice: Subject to any disclaimer, the term of this patent is extended or adjusted under 35 U.S.C. 154(b) by 311 days.

(21) Appl. No.: 16/496,844

(22) PCT Filed: Mar. 29, 2018

(86) PCT No.: PCT/AU2018/050300
§ 371 (c)(1),
(2) Date: Sep. 23, 2019

(87) PCT Pub. No.: WO2018/176104
PCT Pub. Date: Oct. 4, 2018

(65) Prior Publication Data
US 2020/0029807 A1   Jan. 30, 2020

(30) Foreign Application Priority Data

Mar. 30, 2017 (AU) .................. 2017901153

(51) Int. Cl.
*A61B 3/12* (2006.01)
*A61B 3/00* (2006.01)
*A61B 3/14* (2006.01)

(52) U.S. Cl.
CPC .............. *A61B 3/12* (2013.01); *A61B 3/0025* (2013.01); *A61B 3/14* (2013.01)

(58) Field of Classification Search
CPC ............ A61B 3/12; A61B 3/0025; A61B 3/14
(Continued)

(56) References Cited

U.S. PATENT DOCUMENTS

2012/0050674 A1 * 3/2012 Ota ........................ A61B 3/12
351/206
2013/0010260 A1   1/2013 Tumlinson et al.
(Continued)

OTHER PUBLICATIONS

International Search Report dated Jun. 19, 2018, issued by the Australian Patent Office in corresponding PCT Application No. PCT/AU2018/050300, filed Mar. 29, 2018; 4 pages.
(Continued)

*Primary Examiner* — Mohammed A Hasan
(74) *Attorney, Agent, or Firm* — Klarquist Sparkman, LLP (57) ABSTRACT

An ophthalmic imaging apparatus comprising: an illumination light source and an optical assembly for directing light from the light source into an eye of a subject; a photosensor array comprising a plurality of photosensors positioned for acquiring images of portions of a fundus of the eye; an objective lens positioned along an imaging axis intersecting a point on the fundus of the eye wherein the objective lens is positioned for refracting light that has been reflected by the fundus to form an image of the fundus on an image plane of the objective lens such that the image plane is positioned away from the photosensor array; and a microlens array comprising a plurality of microlenses wherein the microlens array is spaced away from and positioned behind the image plane and wherein the microlens array is positioned in between the image plane and the photosensor array such that each microlens in the array projects a different view of the
(Continued)

image formed at the image plane thereby forming an array of elemental images on the photosensor array.

19 Claims, 7 Drawing Sheets

(58) Field of Classification Search
USPC .......................................................... 351/206
See application file for complete search history.

(56) References Cited

U.S. PATENT DOCUMENTS

2014/0347628 A1    11/2014   Corral et al.
2016/0278637 A1*   9/2016    Gao ..................... A61B 3/1015

OTHER PUBLICATIONS

Written Opinion dated Jun. 19, 2018, issued by the Australian Patent Office in corresponding PCT Application No. PCT/AU2018/050300, filed Mar. 29, 2018; 6 pages.

International Preliminary Reporton Patentability dated Nov. 7, 2018, issued by the Australian Patent Office in corresponding PCT Application No. PCT/AU2018/050300, filed Mar. 29, 2018; 16 pages.

* cited by examiner

OPHTHALMIC IMAGING APPARATUS AND SYSTEM

CROSS REFERENCE TO RELATED APPLICATIONS

This is the U.S. National Stage of International Application No. PCT/AU2018/050300, filed Mar. 29, 2018, which was published in English under PCT Article 21(2), which in turn claims the benefit of Australian Application No. 2017901153, filed Mar. 30, 2017. The forgoing applications are incorporated herein in their entirety.

TECHNICAL FIELD

The present invention relates to an ophthalmic imaging apparatus and system particularly for imaging the fundus of a human eye. The invention also relates to a method of ophthalmic imaging.

BACKGROUND

Any references to methods, apparatus or documents of the prior art are not to be taken as constituting any evidence or admission that they formed, or form part of the common general knowledge.

Millions of people all over the world suffer from retinal diseases and as a result of lifestyle changes including increased longevity, this number is increasing. Many diseases can result in partial or total blindness but can be treated effectively if diagnosed early and continuously monitored. Taking a high quality image of the retina suitable for accurate diagnosis requires specialist equipment that is generally bulky, expensive and difficult to transport.

The Retinal Plenoptoscope has been designed to provide wide field images and retinal topography suitable for the diagnosis and monitoring of Age-Related Macular Degeneration (AMD), Glaucoma, Diabetic Retinopathy and Macula Oedema.

The current method of detecting and monitoring many of these diseases is colour and red free fundus imaging. Retinal scans are typically performed with a digital fundus camera which can have fields in excess of 45 degrees and feature sophisticated focussing and eye fixation systems. In recent years, more exotic imaging modalities have become popular such as Optical Coherence Tomography (OCT) which can provide three-dimensional measurements and cross sectional views of retinal structures at very high resolutions (5-15 um). This is particularly useful in the diagnosis and monitoring of Macular Oedema.

Currently available retinal imaging instruments such as digital fundus cameras or OCT units are often large, desk mounted units with significant system complexity and cost devoted to the problem of maintaining reliable imaging conditions, particularly the correct distance of the camera optics to the patient's eyeball and stable eye fixation to properly align the patient's line of sight to that of the camera. If either of these conditions are not met, the resulting image can be out of focus, obscured by flash light glare or exhibit other optical artefacts that reduce the fidelity of the image or obscure significant retinal details. These instruments are typically not easily portable due to their size and complexity.

Accordingly, there is a need to provide an improved ophthalmic imaging system for addressing some of the problems associated with the prior art.

SUMMARY OF THE INVENTION

In the present description, the following terms are employed with the meaning indicated, unless specifically indicated:

Sensor—One or more photosensors, or other type of radiance detectors, arranged in an array.

Elemental image—a section of the image captured on a sensor projected by a single microlens.

Sub-image—elemental image after decoding process.

Light field—a multi-dimensional representation of the positional and directional information associated with all light rays observed in a scene.

Figure 9:
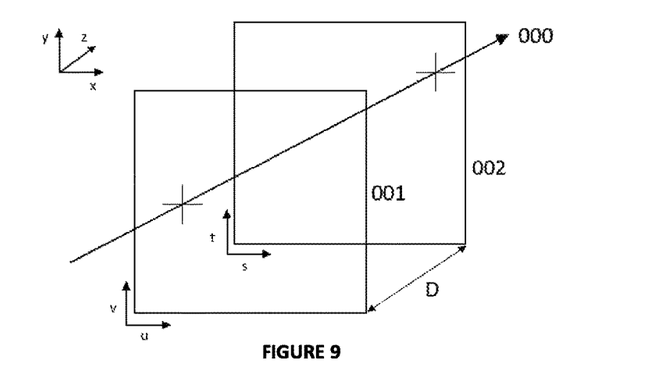
FIG. 9 is an illustration of the 2-plane parameterization model of the 4D light field.

2-plane parameterization—the light field can be defined as a four dimensional array where each ray (000) is categorized by the points at which it intersects two arbitrary parallel planes separated by an arbitrary distance D, as shown in FIG. 9. The light field may then be written in the form $L(u,v,s,t)$, where $(u,v)$ is the point at which each ray (000) intersects the first plane (001), and $(s,t)$ is the point at which the ray (000) intersects the second plane (002).

Objective lens—the optical element or elements in the imaging system closest to the eye.

Relay lens—the optical element or elements in the imaging system closest to the photosensor.

Aperture stop—the physical opening in the imaging optical path that limits the amount of light passing through an optical system.

Entrance pupil—the image of the aperture stop as seen looking into the objective lens from a point on the optical axis of the imaging system.

Exit pupil—the image of the aperture stop as seen looking through the relay lens from a point on the optical axis of the imaging system.

In one aspect, the invention provides an ophthalmic imaging apparatus comprising:
an illumination light source and an optical assembly for directing light from the light source into an eye of a subject;
a photosensor array comprising a plurality of photosensors positioned for acquiring images of portions of a fundus of the eye;
an objective lens positioned along an imaging axis intersecting a point on the fundus of the eye wherein the objective lens is positioned for refracting light that has been reflected by the fundus to form an image of the fundus on an image plane such that the image plane is positioned away from the photosensor array;
a relay lens positioned in between the objective lens and the photosensor for relaying the image plane of the objective lens; and
a microlens array comprising a plurality of microlenses wherein the microlens array is spaced away from and positioned behind the image plane of the objective lens such that the relay lens is positioned in between the objective lens and the microlens array and wherein the microlens array is positioned in between the image plane of the objective lens and the photosensor array such that each microlens in the array projects a different view of the image formed at the image plane of the relay lens thereby forming an array of elemental images on the photosensor array.

In an embodiment, a plurality of contiguous portions of the image formed on the image plane are projected by the array onto the photosensor array.

In an embodiment, each elemental image projected by a corresponding microlens of the array is received on a separate portion of the photosensor array.

In an embodiment, the ophthalmic imaging apparatus further comprises an aperture stop that is positioned along the imaging axis to form an entrance pupil at the pupil of the eye of the subject and to simultaneously project images of the exit pupil in a plane of the photosensor array such that the elemental images formed under each microlens of the microlens array are equal to or smaller than the diameter of each microlens.

Preferably, each elemental image is bounded by a projection of the image of the exit pupil created by the aperture stop seen through the microlens such that the elemental images are contiguous and do not overlap.

In an embodiment, the aperture stop is positioned to allow chief rays of a ray bundle, refracted by the relay lens, that are parallel to the imaging axis to be directed towards the microlens array and produce elemental images of substantially identical size regardless of field angle.

In an embodiment, each microlens of the array is associated with a corresponding set of pixels on the photosensor array.

In an embodiment, each of the microlenses in the microlens array is positioned at a distance b from the photosensor array, wherein f is the focal length of the microlenses, and wherein b is independent of f.

In an embodiment, the aperture stop is positioned in between the objective lens and a relay lens, said relay lens being positioned in between the objective lens and the microlens array and wherein the aperture stop is preferably positioned in spaced relationship relative to the relay lens at a distance that is substantially equivalent to the focal length of the relay lens. Such a configuration provides an image-space telecentric lens system that can produce elemental images of the same size and separation regardless of the field angle.

Preferably, the microlens array is positioned along the imaging axis of the objective lens.

In an embodiment, the ophthalmic imaging apparatus or system further comprises a fixation assembly for axial alignment of the user's eye with the objective lens, the fixation assembly comprising:
 a fixation target whereby during use an image of the target is formed in the retinal plane of the eye by rear illumination of the target by a secondary light source;
 one or more condenser lenses for projecting the light from the secondary light source into the user's eye; and
 one or more beamsplitters for redirecting light received from the one or more condenser lenses to form an image of the fixation target at or near the focal plane of the objective lens.

In an embodiment, the optical assembly for directing light from the light source into the eye further comprises:
 one or more condenser lenses for collimating a beam of light from the illumination source; and
 one or more beamsplitters for redirecting collimated light from the illumination source into the objective lens for illuminating a fundus of the eye.

In an embodiment, the ophthalmic imaging apparatus or system further comprises a processing module to render two-dimensional images by stitching patches of the elemental images projected by each microlens in the array.

In an embodiment, focal depth of the rendered images can be adjusted by varying size of the patches stitched by the processing module.

In an embodiment, the processing module is configured to reconstruct a depth map of the fundus from information relating to the plurality of elemental images projected by one or more of the microlenses of the array.

Preferably, the information relating to the elemental images projected by one or more of the microlenses of the array comprises directional and positional light field information.

Preferably, each of the elemental images projected by the microlens array is processed by the processing module for generating a three dimensional image of the fundus.

In an embodiment, the processing module is further adapted for avoiding glare by selectively ignoring one or more regions of sub-images that include glare.

In an embodiment, the processing module comprises one or more processors and a memory comprising executable program instructions for processing a plurality of the elemental images by selecting separate regions of the plurality of the elemental images in accordance with a pre-determined rule and to obtain a plurality of sub-images and subsequently rendering the sub-images by stitching together said sub-images to obtain a processed image of the fundus.

In an embodiment, the system may be used for reducing or minimizing glare in a processed image of the fundus wherein the processing module comprises one or more processors and a memory comprising executable program instructions for processing a plurality of the elemental images by selecting separate regions of the plurality of the elemental images to obtain a first set of sub-images, selectively ignore one or more portions of subimages from the first set in accordance with a pre-determined rule and to obtain a sub-set of the sub-images and subsequently rendering the sub-images from the sub-set by stitching together said sub-images to obtain a processed image of the fundus.

In another embodiment, the processing module comprises one or more processors and a memory comprising executable program instructions to undertake the steps of obtaining a set of radiance images comprising a plurality of the elemental images; calibrating the radiance images to obtain an intrinsic matrix for the apparatus; and applying the intrinsic matrix to undistort the plurality of elemental images before undertaking subsequent processing steps to form a processed image of the fundus.

In another embodiment, the processing module comprises one or more processors and a memory comprising executable program instructions to receive image data depicting an image of the fundus from a plurality of elemental images; generating at least one data structure from the image data, the at least one data structure comprising data describing a difference in position of at least one object between the plurality of elemental images and wherein the at least one data structure corresponds to at least one region of the image of the fundus; and generating a depth map based on the at least one data structure.

In another aspect, the invention provides a method for ophthalmic imaging of the fundus of an eye, the method comprising the steps of:
 illuminating the eye of a subject by directing light from a light source into the eye of a subject;
 positioning a photosensor array for acquiring images of portions of a fundus of the eye;
 aligning an objective lens along an imaging axis intersecting a point on the fundus of the eye to refracting light that has been reflected by the fundus to form an image of the fundus on an image plane such that the image plane is positioned away from the photosensor array;.

positioning a relay lens in between the objective lens and the photosensor array for relaying the image plane of the objective lens; and positioning a microlens array comprising a plurality of microlenses, said microlens array being spaced away from and behind the image plane of the objective lens such that the relay lens is positioned in between the objective lens and the microlens array and wherein the microlens array is positioned in between the image plane of the objective lens and the photosensor array whereby each microlens of the array projects a different view of the image formed at the image plane of the relay lens thereby forming an array of elemental images on the photosensor array.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF PREFERRED EMBODIMENTS

Figure 1:
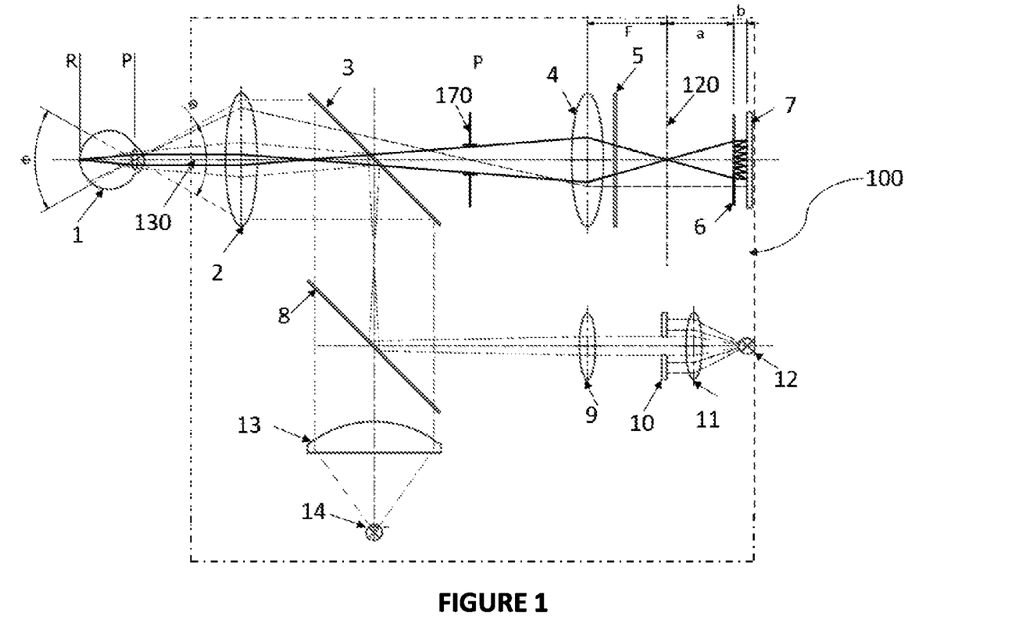
FIG. 1 is a schematic illustration of an ophthalmic imaging apparatus 100 in accordance with an embodiment of the present invention.

Referring to FIG. 1, a schematic diagram of an ophthalmic imaging apparatus 100 is illustrated. The ophthalmic imaging apparatus 100 is provided for capturing a plurality of images of the fundus of a subject's eye 1 in a single view. The term "fundus" refers to a posterior pole of the eyeball and generally comprises the retina, the macula and the optic nerve.

A typical fundus image acquisition method involving the use of the apparatus 100 involves guiding the eye (1) to the correct axial alignment by the use of a fixation assembly that comprises a fixation target (10) whose image is formed at the retinal plane (R). The fixation target is rear illuminated by a low power LED (12) collimated by a lens (11) and its image focussed by lens (9) through a plate beam splitter (8) to a plane, one focal length to the rear of the objective lens (2). This is then projected by the objective lens (2) and as a result, the fixation target (10) is imaged by the eye. To the eye, the fixation target (10) appears at an infinite distance. As a result, the fixation target (10) remains in focus for a relaxed emmetropic eye.

Light for retinal illumination of the eye (1) is provided by an LED source (14) which is focussed by a condenser lens (13) into a collimated beam. This light from the LED source (14) is then directed into the main optical path of the ophthalmic apparatus 100 via a plate beam splitter (3) and through the objective lens (2). The beam directed by the beam splitter (3) is then focussed at or slightly behind the pupil plane of the eye (P) and fans out within the eye to illuminate the retinal surface radially over angle φ. The illumination LED has a 'warm white' radiance of 2700K. This spectrum has a reduced output in the blue range (<450 nm) which is most responsible for the photochemical mechanism of eye damage. The radiant power of the illumination at the pupil plane is significantly reduced compared to that delivered by the LED due to losses in the system, primarily the low reflectance ratio of the beam splitters, and is designed to ensure the safety of the patient as well as maximising signal to noise ratio of the image.

The ophthalmic imaging apparatus 100 comprises a photosensor array 7 positioned for acquiring images of portions of the fundus of the eye (1). The objective lens (2) is positioned along an imaging axis (130) which intersects a point on the fundus of the eye (1). The objective lens (2) is positioned for refracting light that has been reflected by the fundus to form an image of the fundus on an image plane of the objective lens (2). Light reflected from the retina of the emmetropic eye (1) is collimated by the optical elements of the human eye (1) and emitted through the iris of the eye (1). This radiance of the light emitted out of the eye (1) is captured over a wide angle θ by the objective lens (2) and is focused to a plane, specifically an image plane where the image is inverted and relayed via a positive relay lens (4) to a microlens array (6). Signal to noise ratio is improved by filtering excessive objective backscatter using a single linear polarization filter (5). The image plane is positioned away from the photosensor array 7 and the microlens array (comprising a plurality of microlenses) is positioned in between the objective lens (2) and the photosensor array 7 such that each microlens in the array is adapted for projecting at least a portion of the image formed on the image plane 120 of the relay lens (4) onto the photosensor array 7.

In at least some embodiments of the ophthalmic imaging apparatus 100, the microlenses of the microlens array (6) are focused on an image of the fundus formed by the relay lens (4), instead of being afocal, as in conventional plenoptic cameras. The arrangement of the microlens array (6) in the aforementioned configuration of the present ophthalmic imaging apparatus 100 helps in achieving sharper and higher spatial resolution images. The objective lens (2) in combination with the relay lens (4) forms a real image of the fundus in the image plane. The image plane is simply a location in space that can be considered to have an image "in the air" as created by the objective lens (2) and the relay lens (4). The microlenses of the microlens array (6) being focused on the image plane capture the image of the fundus formed at the image plane. Each microlens captures a small area or region of the image at the image plane and maps or projects the captured region onto a corresponding region of the photosensor array 7.

The imaging process of the presently described ophthalmic imaging apparatus 100 may be understood to be comprised of two main steps. The first step involves capturing an image of the fundus of the eye (1) by using the illumination and the objective lens (2) in combination with the relay lens (4) to form an initial image at the image plane. The second subsequent step involves the use of the microlenses in the microlens array (6) to form many small images of the initial image (formed at the image plane) on the photosensor array 7. This arrangement in the present ophthalmic imaging apparatus 100 may be notionally compared to an arrangement comprising two cameras that are operating sequentially. However, the second notional camera (primarily comprising of the microlens array (6) and the photosensor array 7 is actually equivalent to an array of small cameras because each microlens in the microlens array (6) is effectively a little camera that captures a small image from the image plane.

Figure 2:
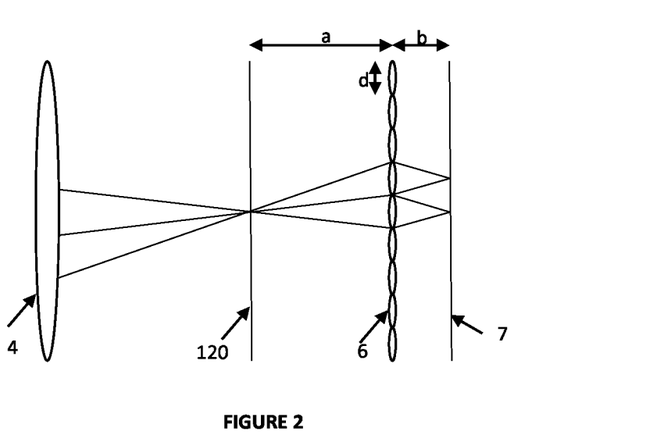
FIG. 2 is an enlarged schematic view of the microlens array (6) and the photosensor array 7 which form a part of the ophthalmic imaging apparatus 100 in a first arrangement whereby the microlens array 6 is positioned away from the relay lens 4 at a position beyond the image plane 120 of the relay lens 4.
Figure 2A:
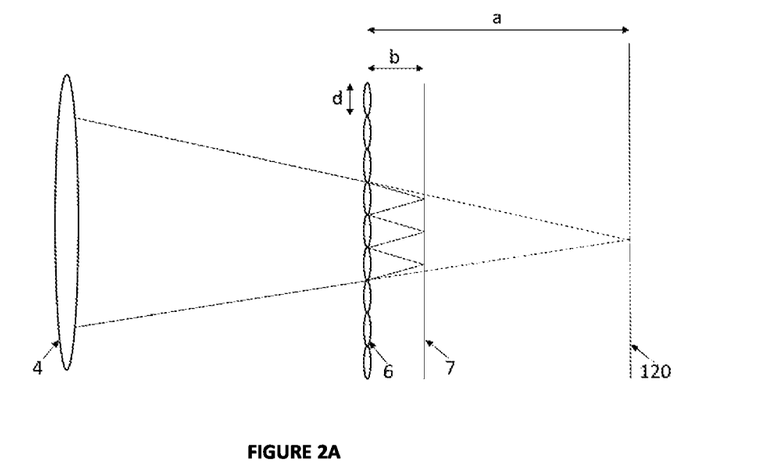
FIG. 2A is an enlarged schematic view of the microlens array (6) and the photosensor array 7 which form a part of the ophthalmic imaging apparatus 100 in a second arrangement whereby the microlens array 6 is positioned in between the relay lens 4 and the image plane 120 of the relay lens 4.

During use, the microlens array (6) samples u×v elemental images at a spatial resolution equivalent to the sensor size in pixels multiplied by the ratio of b/a as shown in FIG. 2. The microlens array (6) may consist of either square microlens elements arranged in an orthogonal pattern or close packed hexagonal elements. The distances b and a are typically larger than the focal length of the microlenses but may be smaller in which case the microlens array samples the virtual image formed by the relay lens (4). FIG. 2 illustrates a first arrangement whereby the microlens array 6 is positioned away from the relay lens 4 at a position beyond the image plane 120 of the relay lens 4. FIG. 2A, on the other hand, illustrates a second arrangement whereby the microlens array 6 is positioned in between the relay lens 4 and the image plane 120 of the relay lens 4.

The elemental images are formed on the photosensor array 7 which may be of any known type such as a charge coupled device (CCD) type or complementary metal-oxide-semiconductor (CMOS). For colour imaging, the image sensor will typically feature a Colour Filter Array to allow separation of RGB colour channels via a demosaicing process but alternative sensor technologies such as Foveon 3× may also be utilised. A monochromatic sensor may also be used in conjunction with visible or infrared illumination or by using burst photography with separate colour channels recorded in quick succession under different wavelength illumination. The resultant radiance captured by the photosensor array 7 in an image therefore consists of a multitude (u×v) of elemental images of size s×t pixels.

Advantageously, an aperture stop 170 is positioned between the objective lens 2 and the relay lens 4. The aperture stop 170 reduces the size of the ray bundle that reaches the photosensor array 7 and is sized such that the extents or boundaries of each of the elemental images formed under the microlenses of the microlens array 6 on the photosensor array 7 are contiguous and without overlap.

Figure 1A:
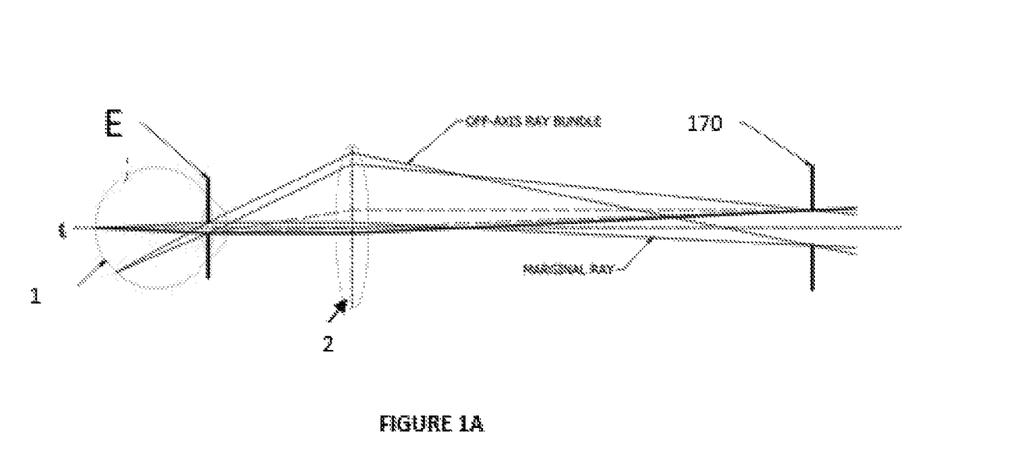
FIG. 1A illustrates the concept of an entrance pupil (E) with reference to the aperture stop 170, the eye of the subject 1 and the objective lens 2.
Figure 1B:
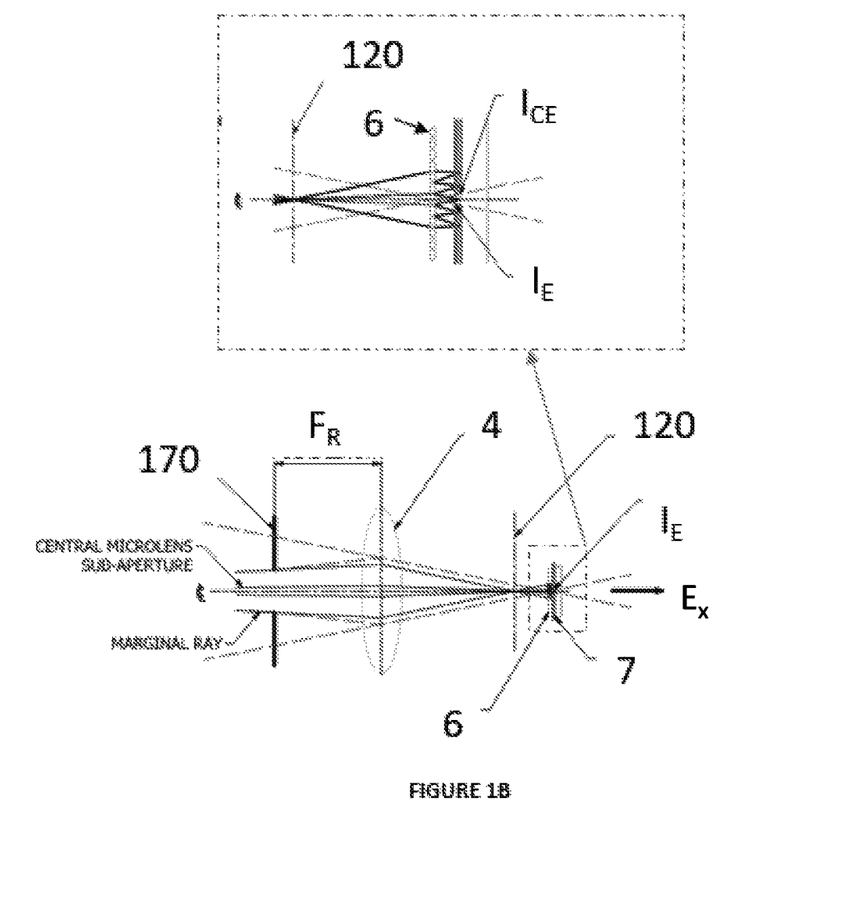
FIG. 1B illustrates a partial view of the ophthalmic imaging apparatus 100, particularly the advantages provided by the positioning of the aperture stop 170.

Referring to FIG. 1B, the aperture stop 170 is positioned along the imaging axis to form an entrance pupil at the pupil of the eye of the subject and to simultaneously project images of the exit pupil in a plane of the photosensor array 7 such that the elemental images formed under each microlens of the microlens array 6 are equal to or smaller than the diameter of each microlens. To avoid excessive vignetting of the elemental images, the aperture stop 170 should be also be sized such that the system entrance pupil is smaller than the minimum pupil of the eye to be imaged. For a non-mydriatic system, this will be around 2-3 mm diameter typically. Furthermore, each elemental image formed by a microlens in the microlens array 6 is bounded by the projected image of the exit pupil created by the aperture stop 170 such that the elemental images are contiguous and do not overlap. The concept of the entrance pupil E has been illustrated in FIG. 1A.

By placing the aperture stop 170 at a distance equal to the focal length ($F_R$) of the relay lens 4 on the image side of the relay lens 4, as shown in FIG. 1B, the chief rays of each ray bundle are projected towards the photosensor array 7 parallel with the imaging axis regardless of field angle. This is referred to as an image space telecentric system and provides some advantages. As the image space ray bundles intersect the microlens array evenly and perpendicularly, there is no angularly dependent distortion of the elemental images due to field angle projection onto the sensor. Additionally, the effects of angular vignetting on image intensity are removed, providing better image quality at large field angles. FIG. 1B illustrates the formation of an image of the Exit pupil ($I_E$) as seen through the central microlens in the microlens array 6. A projection of the central microlens exit pupil image ($I_{CE}$) is also formed on the plane of the photosensor 7. $E_x$ denotes the exit pupil formed for at in infinity.

It is important to note that each elemental image (300) captured by the photosensor array 7 as a result of an individual microlens in the microlens array (6) provides a slightly different perspective view of the fundus of the eye. In other words, each elemental image incident on a predetermined number of pixels of the photosensor array 7 is representative of light passing through an individual microlens in the microlens array (6). By focusing the microlenses of the microlens array (6) on the image produced by the relay lens (4), embodiments of the present ophthalmic system are able to better capture the positional information of the light-field. As will be described in the following sections, a light field rendering method may also be used to render images from light fields captured by photosensor array 7 at a higher spatial resolution than conventional light field rendering techniques.

Figure 8:
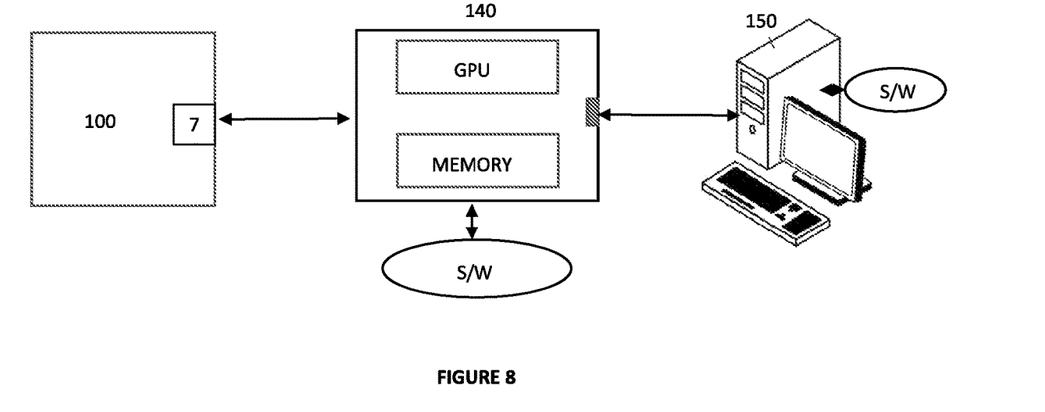
FIG. 8 is a block diagram of an ophthalmic imaging system incorporating a computing unit 140 in communication with an image processing module 150.

Referring to FIG. 8 a block diagram for an ophthalmic imaging system is illustrated. The ophthalmic imaging apparatus 100 may be connected to a first computing unit 140 in communication with the photosensor array 7 of the imaging apparatus 100 for saving the elemental images onto a memory device of the computing unit 140. The computing unit 140 may also be utilised for operating or controlling the imaging apparatus 100. The computing unit 140 may also be in communication with a processing module 150 that may be used for carrying out image processing of the elemental images saved in the memory device of the computing unit 140. The image processing module 150 may comprise one or more processors and a memory comprising executable program instructions for carrying out various image processing functions as will be described in the foregoing sections. The image processing module 150 may be located away from the apparatus 100 and the computing unit 140.

Before being used, the ophthalmic apparatus 100 must undergo a process of factory calibration that allows for adjustments to be made to the captured light field to compensate for distortions caused by the optical system itself. The calibration may be carried out by using the computing unit 140. In this regard, we refer to FIG. 7 which outlines a sequence of steps for operating the ophthalmic apparatus 100. An initial calibration step (701) involves capturing light fields of a specific calibration target from many different poses, and then solving a system of equations to calculate the intrinsic parameters of the ophthalmic system. Given that the system is over-defined, an error term that represents the difference between the projected ray and the actual ray is calculated, this error is minimised using standard optimisation techniques. Additionally, a "white image" will be captured (703) that shows which parts of the sensor correspond to which microlens in the micro lens array 6.

Figure 3:
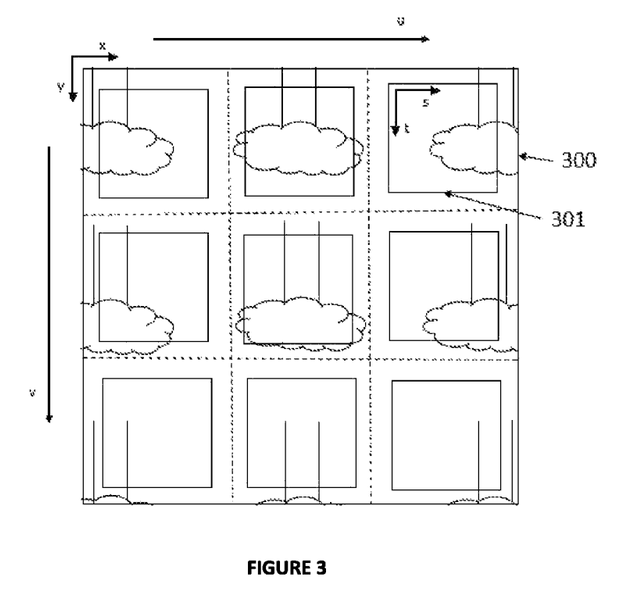
FIG. 3 is an exemplary illustration of the image formed by the microlens array on the sensor showing how elemental images (300) are broken up into sub-images (301).

After a light field has been captured on the sensor (704), it appears as a 2D image comprised of many different elemental images (300). In order to transform these elemental images (300) into the 4D light field, a process called 'decoding' (705) is performed as illustrated in FIG. 3. Decoding consists of transforming each (x,y) coordinate on the raw 2D input into a 4D coordinate (u,v,s,t) consistent with the 2-plane parameterisation method described above. The white image captured during factory calibration is analysed to build a grid that will separate the input image into a series of elemental images (300). The borders of each elemental image (300) are then ignored to create sub-images (301) that improve the quality of the used data, and each point is given its 4D coordinates where (u,v) is the index of the microlens the ray hits, and (s,t) is the location of the point within the microlens the ray hits.

Figure 7:
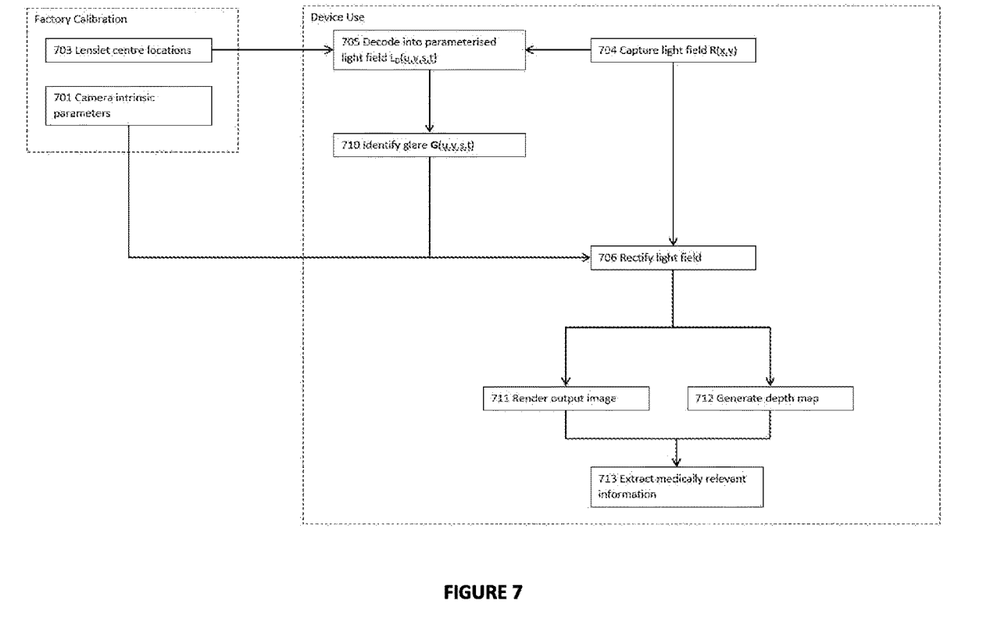
FIG. 7 is a flowchart illustrating various steps involved in the software operation of the ophthalmic imaging apparatus 100.

The light field may be modified to account for distortions caused by the ophthalmic system (100) itself by a process of rectification (706). Rectification (706) is performed by using a matrix of intrinsic parameters calculated during factory calibration (701) to remap the light field into its undistorted form.

Figure 4:
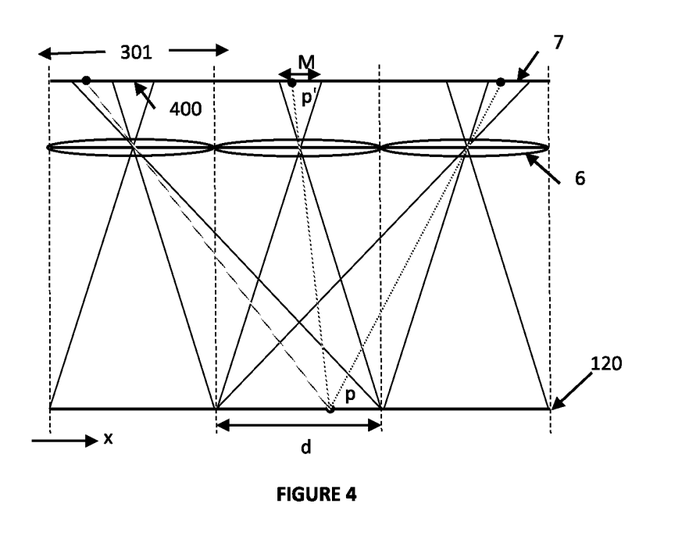
FIG. 4 is a diagram showing a model of how light passes through each microlens (6) to be captured on the sensor 7. The diagram shows only the x-plane of the captured image, but the diagram for the y-plane is similar FIG. 5 is an exemplary illustration of an array of sub-images (301) used for sampling and rendering in order to reduce glare (500).

FIG. 4 is a diagram showing a model of how light passes through each microlens (6) to be captured on the sensor 7. The diagram shows only the x-plane of the captured image, but the diagram for the y-plane is similar.

A method for generating a 2D view of the light field (711) at any specified focal depth is possible using a rendering algorithm in which the microlens array (6) is modelled as an array of pinhole cameras. The following description specifically relates to the first arrangement of the microlens array and the relay lens as shown in FIG. 2. It is important to note that the calculations, as shown below may be varied for other arrangements such as the arrangement shown in FIG. 2A. During rendering (711), a piece of the output image (of size d=size of microlens) that is formed on the image plane (120) is created from a patch (400) (of size M) of the corresponding sub-image (301). Each point p(x,y) in the output image is directly pulled from the sub-image (301) as the corresponding point p'(u,v,s,t) and the two are related by the following equations:

$$u = \left\lfloor \frac{x}{d} \right\rfloor + 1$$

$$v = \left\lfloor \frac{y}{d} \right\rfloor + 1$$

$$s = \frac{d-M}{2} + M - \frac{x - \left\lfloor \frac{x}{d} \right\rfloor d}{d} M$$

$$t = \frac{d-M}{2} + M - \frac{y - \left\lfloor \frac{y}{d} \right\rfloor d}{d} M$$

It is important to note that the point p has corresponding points on multiple sub-images (301) which allows for a reduction in the artifacts in the output render by blending all of these points together to create p throughout the image. The distance between the photosensor array 7 and the microlens array (6) is fixed, but the distance between the microlens array (6) and the image plane (120) may be varied, which in effect is equivalent to changing the size of M (a smaller M corresponds to a larger distance between the microlens array (6) and the image plane (120); thus changing the value of M is equivalent to changing the focal depth of the rendered image. Perspective shift in the image plane can be achieved by shifting the location of the patch (400) within the sub-image (301) (the patch (400) is centered in FIG. 4). The effect of the algorithm, as described herein, may also be conceived as involving a process that carries out a rendering process by taking a small part of each elemental image (300) generated on the photosensor array 7, flipping them about a diagonal axis, enlarging them and putting them all together to create an output image. Additionally, the processing module 150 may also be used for rendering an image with the entire object in focus at once by utilising different patch (400) sizes for each sub-image (301).

Figure 5:
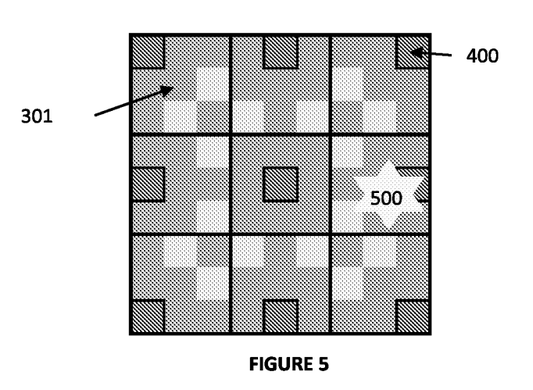

The processing module 150 may also be utilised for removing glare (500) from any rendered images long after the elemental images (300) have been acquired by the ophthalmic apparatus 100, after identifying where glare (500) appears in the light field (710). As each part of the object is sampled in multiple sub-images (301), it is possible to avoid glare (500) by rendering each patch of the final image as a blended combination of its contributing sub-image patches (400) and by selectively ignoring one or more portions of the sub-image patches (400) that include glare (500). FIG. 5 illustrates an exemplary image of a 3×3 array of sub-images (301) and shows how objects are sampled over multiple sub-images (301). A rendered portion is made by combining all of the corresponding patches (400) in the raw data (indicated by the outlined points). Note that glare (500) is represented on the example as a star, and that it covers only some of the available patches (400) used in the combination and can thus be easily avoided through a rendering process (711) carried out by the image processing module 150.

Figure 6:
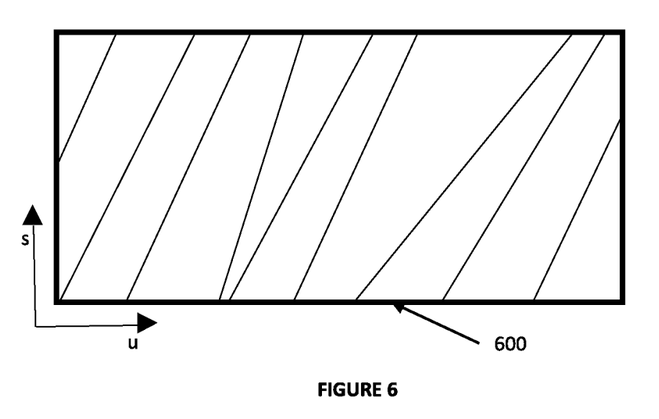
FIG. 6 is an exemplary illustration of an epipolar slice (600) across the s-u plane of the light field.

A captured light field may also be used to create a depth map that allows for 3D reconstruction of the retinal topography of the eye being examined. The process (712) used to calculate a depth map of the light field involves generating depth from motion, which is done through an examination of epipolar images (600) created from the light field. An epipolar image (600) is an image that tracks the motion of objects in a scene as the camera pans in one direction, which is performed virtually in the plenoptic camera. The resultant image comprises a set of sloped lines corresponding to each feature in the scene, as shown in FIG. 6, with the magnitude of the slope relative to the distance from the camera to the feature. Thus, a depth map can be created by calculating the gradient of each point in the light field in its corresponding epipolar image (600).

The use of the ophthalmic imaging apparatus 100 can provide improvements over conventional digital fundus cameras in the speed and reliability of image focus and acquisition. Due to simplification of the focusing and alignment components of the apparatus 100, cost and complexity can be reduced which results in a robust, inexpensive and highly portable system. Additional novel features include the ability to synthetically refocus images post acquisition (711), remove glare (710), and create depth maps or 3D renders of retinal surface features (712).

The processing module 150 may also utilize software to render views (711) of the fundus in any other manner that is useful to a medical professional in the identification of medically relevant information (713), for example the generation of a stereo pair is a trivial software operation (two rendered images at the same focal depth but different perspectives). The processing module 150 may also be used to create a data set for use in training a deep learning algorithm. The deep learning algorithm would be capable of identifying glare in the light field (710) and examining the 4D light field directly to extract relevant medical details (713).

The ability to refocus an image at a later stage (post shot) is especially useful for retinal imaging as maintaining adequate focus and alignment of a living, moving eye can be difficult to achieve, especially with portable field equipment. Overcoming such a shortcoming of previously known ophthalmic imaging systems is one of the major advantages of the presently described ophthalmic imaging apparatus 100. Presently available ophthalmic imaging systems require patient head restraint and axis positioning actuators to achieve consistent results.

In addition, the present ophthalmic apparatus 100 also allows the use of deep learning techniques trained on 4D light field data sets which promises improvements in the resilience of automated disease detection and diagnosis to noise and image acquisition error. The apparatus 100 is also likely to provide a robust, low cost platform for remote imaging and diagnostic telemedicine. Therefore, the apparatus 100 provides an improved alternative to current retinal imaging modalities, replacing complex, expensive retinal imaging equipment with a simpler, more portable, lower cost system.

Unlike presently available imaging systems, the ophthalmic imaging apparatus 100 is useful for 3D reconstruction of retinal topography which allows the operator to diagnose more conditions with one piece of equipment. The apparatus 100 also provides increased reliability of equipment through simplification of an optical system and removal of a mechanical alignment system. The apparatus 100 provides a higher percentage of usable shots due to glare removal and ability to refocus images post acquisition thus reducing overall operating expenditure. The apparatus 100 is also useful because of reduction of componentry by replacing multiple optical-mechanical components with a single microlens array (6).

The applicants envision using the ophthalmic imaging apparatus 100 for use as both handheld and desk mounted ophthalmic imaging systems depending on market requirements. The flowchart in FIG. 7 shows the standard flow of the associated software program.

In compliance with the statute, the invention has been described in language more or less specific to structural or methodical features. The term "comprises" and its variations, such as "comprising" and "comprised of" is used throughout in an inclusive sense and not to the exclusion of any additional features.

It is to be understood that the invention is not limited to specific features shown or described since the means herein described comprises preferred forms of putting the invention into effect.

The invention is, therefore, claimed in any of its forms or modifications within the proper scope of the appended claims appropriately interpreted by those skilled in the art.

Throughout the specification and claims (if present), unless the context requires otherwise, the term "substantially" or "about" will be understood to not be limited to the value for the range qualified by the terms.

Any embodiment of the invention is meant to be illustrative only and is not meant to be limiting to the invention. Therefore, it should be appreciated that various other changes and modifications can be made to any embodiment described without departing from the spirit and scope of the invention.

The claims defining the invention are as follows:

1. An ophthalmic imaging apparatus comprising:
   an illumination light source and an optical assembly for directing light from the light source into an eye of a subject;
   a photosensor array comprising a plurality of photosensors positioned for acquiring images of portions of a fundus of the eye;
   an objective lens positioned along an imaging axis intersecting a point on the fundus of the eye wherein the objective lens is positioned for refracting light that has been reflected by the fundus to form an image of the fundus on an image plane of the objective lens such that the image plane is positioned away from the photosensor array;
   a relay lens positioned in between the objective lens and the photosensor array for relaying the image plane of the objective lens; and
   a microlens array comprising a plurality of microlenses wherein the microlens array is spaced away from and positioned behind the image plane of the objective lens such that the relay lens is positioned in between the objective lens and the microlens array and wherein the microlens array is positioned in between the image plane of the objective lens and the photosensor array and spaced away from an image plane of the relay lens such that each microlens in the array projects a different view of an image formed at the image plane of the relay lens thereby forming an array of elemental images on the photosensor array; and
   an aperture stop that is positioned along the imaging axis to form an entrance pupil at a pupil of the eye of the subject and to simultaneously project images of an exit pupil in a plane of the photosensor array such that the elemental images formed under each microlens of the microlens array are equal to or smaller than the diameter of each microlens.

2. An ophthalmic imaging apparatus in accordance with claim 1 wherein a plurality of contiguous portions of the image formed on the image plane of the relay lens are projected by the array onto the photosensor array.

3. An ophthalmic imaging apparatus in accordance with claim 2 wherein during use each elemental image projected by a corresponding microlens of the array is received on a separate portion of the photosensor array.

4. An ophthalmic imaging apparatus in accordance with claim 1 wherein each elemental image is bounded by the projected image of the exit pupil created by the aperture stop such that the elemental images are contiguous and do not overlap.

5. An ophthalmic imaging apparatus in accordance with claim 1 wherein the aperture stop is positioned to allow chief rays of a ray bundle, refracted by the relay lens, that are parallel to the imaging axis to be directed towards the microlens array and produce elemental images of substantially identical size and separation regardless of field angle.

6. An ophthalmic imaging apparatus in accordance with claim 1 wherein each microlens of the microlens array is associated with a corresponding set of pixels on the photosensor array.

7. An ophthalmic imaging apparatus in accordance with claim 1 wherein each of the microlenses in the microlens array is positioned at a distance b from the photosensor array, wherein f is a focal length of the microlenses, and wherein b is independent off.

8. An ophthalmic imaging apparatus in accordance with claim 1 wherein the microlens array is positioned along the imaging axis of the objective lens.

9. An ophthalmic imaging apparatus in accordance with claim 1 further comprising a fixation assembly for axial alignment of the user's eye with the objective lens, the fixation assembly comprising:
a fixation target whereby during use an image of the target is formed in the retinal plane of the eye by rear illumination of the target by a secondary light source;
one or more condenser lenses for projecting the light from the secondary light source into the user's eye; and
one or more beamsplitters for redirecting light received from the one or more condenser lenses to from an image of the fixation target at or near the focal plane of the objective lens.

10. An ophthalmic imaging apparatus in accordance with claim 1 wherein the optical assembly for directing light from the light source into the eye further comprises:
one or more condenser lenses for collimating a beam of light from the illumination source; and
one or more beamsplitters for redirecting collimated light from the illumination source into the objective lens for illuminating the fundus of the eye.

11. An ophthalmic imaging system comprising the apparatus in accordance with claim 1 further comprising a processing module to render two-dimensional images by stitching patches of the elemental images projected by each microlens in the array.

12. An ophthalmic imaging system in accordance with claim 11 wherein focal depth of the rendered images can be adjusted by varying size of the patches of the elemental images stitched by the processing module.

13. An ophthalmic imaging system in accordance with claim 11 wherein the processing module is configured to reconstruct a depth map of the fundus from information relating to a plurality of the elemental images projected by one or more of the microlenses of the microlens array.

14. An ophthalmic imaging system in accordance with 11 wherein the information relating to the plurality of the elemental images projected by the microlenses of the array comprises directional and positional light field information.

15. An ophthalmic imaging system in accordance with claim 11 wherein the processing module comprises one or more processors and a memory comprising executable program instructions for processing a plurality of the elemental images by selecting separate regions of the plurality of the elemental images in accordance with a pre-determined rule and to obtain a plurality of sub-images and subsequently rendering the sub-images by stitching together said sub-images to obtain a processed image of the fundus.

16. An ophthalmic imaging system in accordance with claim 11 for reducing or minimizing glare in a processed image of the fundus wherein the processing module comprises one or more processors and a memory comprising executable program instructions for processing a plurality of the elemental images by selecting separate regions of the plurality of the elemental images to obtain a first set of sub-images, selectively ignore one or more portions of sub-images in accordance with a pre-determined rule and to obtain a sub-set of the sub-images and subsequently rendering the sub-images from the sub-set by stitching together said sub-images to obtain a processed image of the fundus.

17. An ophthalmic imaging system in accordance with claim 11 wherein the processing module comprises one or more processors and a memory comprising executable program instructions to undertake the steps of obtaining a set of radiance images comprising a plurality of the elemental images; calibrating the radiance images to obtain an intrinsic matrix for the apparatus; and applying the intrinsic matrix to undistort the plurality of elemental images before undertaking subsequent processing steps to form a processed image of the fundus.

18. An ophthalmic imaging system in accordance with claim 11 wherein the processing module comprises one or more processors and a memory comprising executable program instructions to receive image data depicting an image of the fundus from a plurality of elemental images; generating at least one data structure from the image data, the at least one data structure comprising data describing a difference in position of at least one object between the plurality of elemental images and wherein the at least one data structure corresponds to at least one region of the image of the fundus; and generating a depth map based on the at least one data structure.

19. A method for ophthalmic imaging of the fundus of an eye of a subject, the method comprising the steps of:
illuminating the eye of the subject by directing light from a light source into the eye of a subject;
positioning a photosensor array for acquiring images of portions of a fundus of the eye;
aligning an objective lens along an imaging axis intersecting a point on the fundus of the eye to refracting light that has been reflected by the fundus to form an image of the fundus on an image plane such that the image plane is positioned away from the photosensor array;
positioning a relay lens in between the objective lens and the photosensor array for relaying the image plane of the objective lens; and
positioning a microlens array comprising a plurality of microlenses, said microlens array being spaced away from and behind the image plane of the objective lens such that the relay lens is positioned in between the objective lens and the rnicrolens array and wherein the microlens array is positioned in between the image plane of the objective lens and the photosensor array and spaced away from an image plane of the relay lens whereby each microlens of the array projects a different view of the image formed at the image plane of the relay lens thereby forming an array of elemental images on the photosensor array; and
positioning an aperture stop along the imaging axis to form an entrance pupil at a pupil of the eye of the subject and to simultaneously project images of an exit pupil in a plane of the photosensor array such that the elemental images formed under each microlens of the microlens array are equal to or smaller than the diameter of each microlens.

* * * * *

UNITED STATES PATENT AND TRADEMARK OFFICE
CERTIFICATE OF CORRECTION

| | | |
|---|---|---|
| PATENT NO. | : 11,337,607 B2 | Page 1 of 1 |
| APPLICATION NO. | : 16/496844 | |
| DATED | : May 24, 2022 | |
| INVENTOR(S) | : Jaiprakash et al. | |

It is certified that error appears in the above-identified patent and that said Letters Patent is hereby corrected as shown below:

On the Title Page

Item (57), Line 9 of the Abstract, "the fund us on an image plane" should read --the fundus on an image plane--.

In the Claims

Column 13, Line 18, "wherein b is independent off." should read --wherein b is independent of f.--.

Column 13, Line 32, "to from an" should read --to form an--.

Signed and Sealed this
Twenty-sixth Day of July, 2022

Katherine Kelly Vidal
*Director of the United States Patent and Trademark Office*